(12) United States Patent
Parrott et al.

(10) Patent No.: US 11,639,431 B2
(45) Date of Patent: *May 2, 2023

(54) PROCESS AND SYSTEM FOR DEPOLYMERIZING PLASTIC

(71) Applicant: Premirr Plastics Inc., Chapel Hill, NC (US)

(72) Inventors: Matthew Craig Parrott, Chapel Hill, NC (US); James Christopher Luft, Chapel Hill, NC (US); Donald B. Shuping, Pittsboro, NC (US); Michael Dean Mattiace, Chapel Hill, NC (US)

(73) Assignee: Premirr Plastics Inc., Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/157,418

(22) Filed: Jan. 25, 2021

(65) Prior Publication Data

US 2021/0230391 A1 Jul. 29, 2021

Related U.S. Application Data

(60) Provisional application No. 62/964,948, filed on Jan. 23, 2020, provisional application No. 62/964,957, filed on Jan. 23, 2020.

(51) Int. Cl.
*C08J 11/12* (2006.01)
*B01J 6/00* (2006.01)
*C07C 67/293* (2006.01)

(52) U.S. Cl.
CPC ............ *C08J 11/12* (2013.01); *B01J 6/008* (2013.01); *C07C 67/293* (2013.01); *C08J 2367/02* (2013.01)

(58) Field of Classification Search
CPC ............ C08J 11/12; C08J 11/14; C08J 11/18; C08J 11/24; C08J 2367/02; B01J 6/008
See application file for complete search history.

(56) References Cited

U.S. PATENT DOCUMENTS 3,701,741 A * 10/1972 Meyer .................... C08G 63/90
521/48.5
5,481,024 A * 1/1996 Hertenstein .............. B01J 31/04
560/78

(Continued)

FOREIGN PATENT DOCUMENTS

| EP | 1134211 A1 | 9/2001 | |
| JP | 202-167468 | * 6/2002 | ............ C07B 61/00 |
| WO | 2017087752 A1 | 5/2017 | |

OTHER PUBLICATIONS

JP2002-167468, Miyamoto Masakazu, Recovery method of active ingredient from polyester film scrap, English translation, 7 pages (Year: 2002).*

(Continued)

*Primary Examiner* — Yate' K Cutliff
(74) *Attorney, Agent, or Firm* — Jones Walker LLP (57) ABSTRACT

A continuous flow process and system for depolymerizing plastic. A heterogeneous mixture of solid plastic particles, a solvent, and a catalyst are pumped continuously through a heating zone at a flow rate resulting in a particle speed sufficient to keep the plastic particles in suspension. The heterogeneous mixture is heated in the heating zone and maintained in a hold zone to complete depolymerization of the mixture into a homogeneous solution containing a liquefied reaction product. The homogeneous solution is cooled to solidify and precipitate a solid reaction product. The solid reaction product is separated from the solvent to (Continued)

be recycled. Contaminants are removed from the solvent, and the solvent is recirculated for use as a constituent of the heterogeneous mixture.

26 Claims, 3 Drawing Sheets

(56) References Cited

U.S. PATENT DOCUMENTS

| | | | | |
|---|---|---|---|---|
| 6,410,607 B1* | 6/2002 | Ekart | ................... | C08G 63/90 521/48.5 |
| 6,916,936 B2* | 7/2005 | Hedrick | ............... | C07D 233/04 560/216 |
| 10,508,186 B2 | 12/2019 | Parrott | | |
| 10,858,493 B2 | 12/2020 | Parrott | | |
| 2005/0096482 A1* | 5/2005 | Tamada | ................... | C08J 11/24 560/89 |
| 2015/0290840 A1* | 10/2015 | Boisart | ................. | C08J 11/105 435/142 |
| 2020/0262997 A1* | 8/2020 | Sasson | ................... | C08J 11/12 |
| 2021/0047495 A1 | 2/2021 | Parrott | | |

OTHER PUBLICATIONS

George, N. et al., Recent developments in the chemical recycling of postconsumer poly(ethylene terephthalate) waste, Industrial & Engineering Chemistry Research, 53, pp. 14185-14198 (Year: 2014).*

Lopez-Fonseca, R., et al., Chemical recycling of post-consumer PET wastes by glycolysis in the presence of metal salts, Polymer Degradation and Stability, 95, pp. 1022-1028 (Year: 2010).*

EPO as ISA, PCT/US2021/014896, PCT International Search Report, dated Jun. 9, 2021, 4 pages.

Achilias, Dimitris S., Polymer Degradation Under Microwave Irradiation, Adv Polym Sci (2016) 274: 309-346 Springer International Publishing Switzerland 2014, published online Nov. 2, 2014.

Geyer, B., Lorenz, G., Kandelbauer, A., Recycling of polyfethylene terephthalate)—A review focusing on chemical methods, eXPRESS Polymer Letters vol. 10, No. 7 (2016) 559-586, Nov. 27, 2015, revised Feb. 8, 2016.

* cited by examiner

PROCESS AND SYSTEM FOR DEPOLYMERIZING PLASTIC

CROSS REFERENCE TO RELATED APPLICATIONS

This application claims priority to U.S. Provisional Application No. 62/964,948, filed on Jan. 23, 2020, and to U.S. Provisional Application No. 62/964,957, filed on Jan. 23, 2020, each of which is hereby incorporated by reference in its entirety.

BACKGROUND

The invention relates generally to the depolymerization of resin, plastic, or polymer. More particularly, it relates to the depolymerization of plastic in a continuous flow-through process.

The invention also relates generally to the dissolution and subsequent purification of resin, plastic, or polymer, specifically in a continuous process.

Plastic, especially polyesters such as polyethylene terephthalate (PET or PETE), is conventionally depolymerized in large reaction vessels usually equipped with a heating jacket and an agitator. The depolymerization reaction is sequestered in the vessel until depolymerization is complete. After depolymerization the vessel is emptied and then refilled. Each batch is heated to speed up depolymerization and then cooled to produce viable raw material for new polymers. The batch process typically takes between 20 min and 800 min. Continuous operation is simulated by sequentially emptying and refilling a group of reaction vessels in round-robin fashion. The constant need to fill, heat, cool, empty, and repeat wastes energy and requires additional equipment to maintain the illusion of actual continuous flow in a parallel batch process.

Similarly, plastic is conventionally dissolved in large reaction vessels. The dissolution is sequestered in the vessels until complete. After, the vessels are emptied and refilled. Each batch is heated to speed up dissolution, purified, and cooled to precipitate virgin-like material for new polymers. These batch dissolution processes also waste energy.

SUMMARY

A process embodying features of the invention for depolymerizing plastic comprises: (a) continuously flowing a mixture containing solid plastic particles in a solvent through a line in a heating chamber at a particle speed sufficient to maintain suspension of the plastic particles in the solvent and to prevent the plastic particles from agglomerating and clogging the line; and (b) transferring heat through the line in the heating chamber to heat the mixture to a reaction temperature to start the depolymerization of the plastic particles in the solvent into a homogeneous solution including a liquefied reaction product.

A system embodying features of the invention for the continuous depolymerization of plastic comprises a pump operating at a flow rate; a line through which the pump continuously feeds a heterogeneous mixture including solid plastic particles in a solvent at a particle speed; and a heating zone raising the temperature of the heterogeneous mixture flowing through the line to a reaction temperature of at least 150° C. The conversion of the heterogeneous mixture containing the solid plastic particles into a homogeneous solution containing a liquefied reaction product is started in the heating zone.

A process embodying features of the invention for the dissolution of plastic comprises: (a) continuously flowing a mixture containing solid plastic particles in a solvent through a line in a heating chamber at a particle speed sufficient to maintain suspension of the plastic particles in the solvent and to prevent the plastic particles from agglomerating and clogging the line; and (b) transferring heat through the line in the heating chamber to heat the mixture to a temperature to start the dissolution of the plastic particles in the solvent into a homogeneous solution containing a liquefied plastic.

A system embodying features of the invention for the continuous dissolution of plastic comprises a pump operating at a flow rate; a line through which the pump continuously feeds a heterogeneous mixture including solid plastic particles in a solvent at a particle speed; and a heating zone raising the temperature of the heterogeneous mixture flowing through the line to at least 100° C. The conversion of the heterogeneous mixture containing the solid plastic particles into a homogeneous solution containing a liquefied plastic is started in the heating zone.

DETAILED DESCRIPTION

Figure 1:
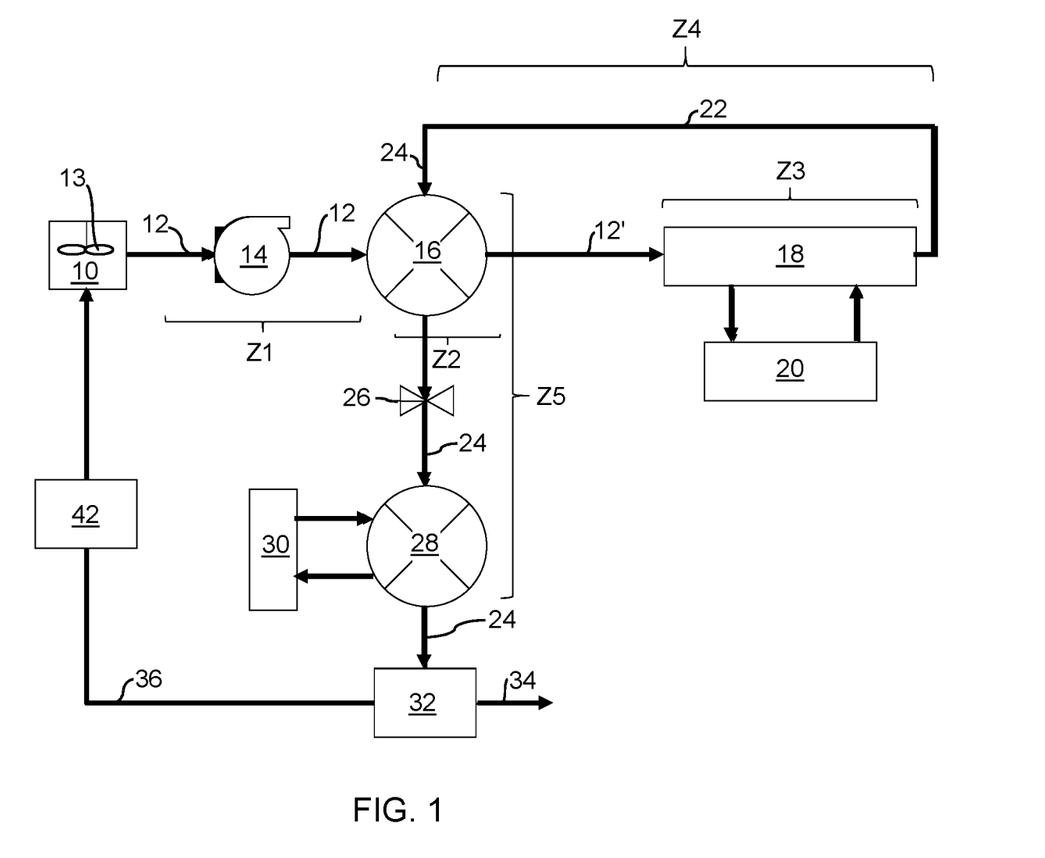
FIG. 1 is a block diagram of a system embodying features of the invention for depolymerizing plastic and for the dissolution of plastic.

A system and a process for depolymerizing plastic is shown in FIG. 1. The system and process shown in FIG. 1 may also be used to dissolve plastic. The system and process may be used with various plastics such as, but not limited to, PET, modified PET, PET blends, polyethylene naphthalate (PEN), polybutylene terephthalate (PBT), polyethylene terephthalate glycol (PET-G), polylactic acid (PLA), poly(glycolic acid) (PGA), poly D,L-lactic-co-glycolic acid (PLGA), polyethylene 2,5-furandicarboxylate (PEF), copolyesters, polycarbonates, polyamides (nylon), polyurethanes and combinations and blends. Reaction products yielded by depolymerization of these plastics include, but are not limited to: (bis (2-hydroxyethyl) terephthalate (BHET), 2-hydroxyethyl terephthalic acid (MHET), dimethyl terephthalate (DMT), terephthalic acid (TA), (bis (2-hydroxyethyl) naphthalate (BHEN), (bis (2-hydroxyethyl) Furanoate (BHEF) their respective oligomers, acids, half-esters, or mixed esters. Additionally, reaction products may include dioctyl terephthalate (DOTP), diisobutyl terephthalate (DITP), dibutyl terephthalate (DBTP), bisphenol A (BPA), lactates, bis (2-hydroxyethyl) terephthalamide (BHETA), and other terephthalamides.

Solid plastic particles of waste material, in the form of flakes, fines, grain, granules, granola, lumps, chunks, and/or powder, are mixed with a solvent and a catalyst in a mixer 10 to produce a heterogeneous mixture 12. The mixer 10 can use an agitator, such as a propeller 13, stirrer, or other agitator or a recirculating solvent to do the mixing. Or the mixture can be premixed. Examples of solvents are, but not limited to, ethylene glycol (EG), diethylene glycol (DEG), glycol ethers, methanol, ethanol, propanol, butanol, 2-ethyl hexanol, tetramethyl cyclobutanediol (CBDM), cyclohexanedimethanol (CHDM), alcohols, ethanol amine, ionic liquids, polar protic solvents, polar aprotic solvents, and water. Examples of suitable catalysts include but not limited to: zinc salts; zinc acetate; zinc chloride; titanium salts; titanium (IV) isopropoxide; titanium (IV) n-butoxide; manganese salts; magnesium salts; sodium hydroxide; potassium hydroxide; 1, 5, 7-Triazabicyclo [4.4.0] dec-5-ene (TBD); 1, 8-Diazabicyclo [5.4.0] undec-7-ene (DBU); magnesium acetate, 4-dimethylaminopyridine (DMAP); amine; trialkyl amine; and combinations of those catalysts. The heterogeneous mixture 12 is pumped through a series of connected lines, such as tubes or pipes, by a pump 14. No agitator, auger, or extruder is needed to advance the mixture through the system. The pump 14 operates at a flow rate great enough to move the mixture 12 through the system with a particle speed great enough to maintain the PET particles suspended in the solvent and to prevent the particles from agglomerating and clogging the lines. By operating continuously without stopping, the pump 14 flows the heterogeneous mixture through the system at a steady rate that makes the conversion of PET into liquified reaction product a function of position within the system rather than a function of time—as in batch systems.

A preheating heat exchanger (preheater) 16 is used to preheat the heterogeneous mixture 12. The preheater 16 can heat the heterogeneous mixture 12 by a heat source, such as a flame, steam, hot-oil or a circulated heat transfer fluid. Or preferably, the hot homogeneous solution containing the liquified reaction product after the depolymerization reaction can be used in the preheater 16 to transfer heat to the heterogeneous mixture and, in the process, cool itself down. The preheating heat exchanger 16 can include a tube-in-shell, tubes-in-shell, coil-in-shell, tube-in-tube, jacketed piping (i.e., a jacket around an inner pipe), platular, plate-and-shell, or plate-and-frame heat exchanger.

The preheated heterogeneous mixture 12' flows continuously into and through a downstream heating chamber 18 in which depolymerization starts. The heating chamber 18 may be realized as a reactor heat exchanger that raises the temperature of the heterogeneous mixture to a reaction temperature sufficient for the depolymerization of the solid plastic particles, preferably at least 150° C., more preferably at least 230° C. The reaction temperature may be within 20° C. of the melting point of the plastic particles in the heterogeneous mixture. For example, the heating chamber 18 may heat the heterogeneous mixture to a reaction temperature in the range of 230° C. to 270° C., preferably about 250° C., when the heterogeneous mixture contains PET, which has a melting point of 250° C. In another example, the heating chamber 18 may heat the heterogeneous mixture to a reaction temperature of about 150° C. when the heterogeneous mixture contains PLA, which have melting points of 150° C. The heating chamber 18 in heating zone Z3 can include a tube-in-shell, tubes-in-shell, coil-in-shell, tube-in-tube, jacketed piping (i.e., a jacket around an inner pipe), platular, plate-and-shell, or plate-and-frame heat exchanger.

The heterogeneous mixture is heated in the reaction heat exchanger 18 by a heat source 20. The heat source 20 may directly heat the heterogeneous mixture with microwave radiation, direct flame, electrically heated pipe, inductively heated pipe, geothermal, magnon-drag thermoelectricity, or ohmically, as a few examples. Or the heat source 20 may indirectly heat the heterogeneous mixture by directly heating a heat transfer fluid external to the heating chamber 18. Examples of suitable transfer fluids are hot oil, a thermal fluid, a molten salt, and steam. The heated heat transfer fluid is then pumped past the line containing the heterogeneous mixture in the heating chamber 18. Heat is transferred from the heat transfer fluid to the heterogeneous mixture to start depolymerization. The heterogeneous mixture flowing through the heating chamber 18 is not contacted directly by the heat transfer fluid.

A hold tube 22 after the heating chamber 18 maintains the reaction temperature for at least one minute to complete the conversion of the heterogeneous mixture containing PET to a homogeneous solution 24 containing the liquified reaction product. The hold tube 22 may be realized by an insulated spool or coil of pipe or tube or as a jacketed pipe or vessel. Or the hold tube can be part of the heating chamber rather than a stand-alone component. The reaction is completed in the hold tube. The exiting homogeneous solution contains the solvent, the spent catalyst, and depolymerized PET in the form of a liquefied reaction product that typically includes monomers, oligomers, and/or minor side-products from the reaction (e.g. half-esters, half-amides, mixed esters, mixed amides).

The homogeneous solution 24 is pumped continuously through the optional preheating heat exchanger 16 to cool itself and preheat the incoming heterogeneous mixture 12. A backpressure regulator 26 maintains a system pressure, e.g., 50 psi or 100 psi to 400 psi, above the vapor pressure of the solvent at the reaction temperature.

After flowing through the backpressure regulator 26, the homogeneous solution 24 flows through an optional chilling heat exchanger (chiller) 28 that uses cold water or other cooling heat transfer fluid from a chilled reservoir 30 to remove any excess heat that the preheater 16 did not reclaim. In a preferred embodiment, the homogeneous solution 24 is cooled in the chilling heat exchanger 28 to a temperature below 50° C.

After the solution is cooled, it is poured into precipitation or crystallization tanks and cooled until the liquefied reaction product precipitates as a solid reaction product 34, such as the composition described in Table 1. In one embodiment, the cooled homogeneous solution may be settled at room temperature for a time between about 0.5 hour and 100 hours to allow the liquefied reaction product to solidify into the solid reaction product 34. The solvent is then decanted, filtered, centrifuged or distilled away from the solid reaction product. The solid reaction product may be subsequently filter-pressed to further separate it from any remaining solvent. The decanting, filtration, centrifugation or distillation of solvent, followed by the pressing to separate the solid reaction product 34 in the solution 24 from the solvent 36 is represented in FIG. 1 by a separator 32. The solid reaction product 34 can later be used to form "new" PET, specialty polyesters, monomers, and/or product additives all from recycled content.

The separated solvent 36 is recirculated back to the mixer 10 for reuse. An optional solvent cleaning, purification or regeneration step may be required to remove reaction contaminants from the solvent feeding the subsequent heterogeneous mixture 12. Reaction contaminants may include solid particulate, ionic salts, anions, cations, spent catalyst, dyes, adhesives, components from blends, fillers and/or decomposed solvent. Contamination removal 42 may occur by passing the separated solvent 36 through filters and/or over sorbents such as activated charcoal, ion exchange resin, diatomaceous earth, fullers earth, sand, zeolites, clay, silica, alumina, oxides, size exclusion and/or tangential flow filtration. Contamination removal 42 of solvent 36 may be an in-line or off-line process. Contamination removal 42 may occur at the separated solvent step 36 or at the homogeneous solution step 24.

Thus, the system moves the heterogeneous mixture 12 through four zones: Z1—a cold entry zone in which the mixture is fed into the system by the pump 14; Z2—a preheating zone in which the mixture is heated in the preheater 16; Z3—a heating zone in which the mixture is heated to raise its temperature to the reaction temperature; and Z4—a hold zone in which the mixture is maintained at the reaction temperature to complete the conversion of the heterogeneous mixture into the homogeneous solution 24. The homogeneous solution 24 is moved through a cooling zone Z5 in which the homogeneous solution is cooled in the chiller 28 or by the transfer of heat to the incoming heterogeneous mixture 12 in the preheater 16. The pump 14 maintains a continuous flow rate through the system that ensures a particle speed of the heterogeneous mixture great enough to keep the particles in suspension. In that way the plastic particles do not settle in the lines and clog the system.

The size of plastic particles pumped through the system can vary, but they are typically between 0.1 μm and 20,000 μm in at least one dimension. To maintain the particles in suspension, the flow rate of the pump 14 is set to ensure a particle speed of at least 30 cm/s through the system. Particle speeds above 30 cm/s provide a safety margin. In some embodiments, the flow rate is set to provide a particle speed of about 100 cm/s. In other embodiments, the flow rate is set to provide a particle speed of about 500 cm/s. The pump flow rate is set equal to the product of the desired particle speed and the cross-sectional area of the lines (pipes or tubes) through which the mixture is pumped. If mixers are installed in the lines between the pump 14 and the regulator 26, lower particle speeds are possible.

In the heating zone Z3, the heating chamber 18 raises the temperature to the reaction temperature or higher to start the depolymerization reaction, which is completed in the hold zone Z4. The length L of the hold tube 22 in the hold zone Z4 depends on its cross-sectional area A, the pump's flow rate Q, and the hold time T required at the reaction temperature to complete the reaction: $L=QT/A$. The hold time can range from 5 min to 10 min or even from 1 min to 60 min. The diameter of the lines running through the zones is 1 cm to 10 cm, but can be as great as 100 cm. If jacketed piping is used, the inner diameter of the inner pipe may be between 1 cm and 100 cm, and the diameter of the jacket may range from 1.1 to 5.0 times the diameter of the inner pipe through which the mixture is pumped.

The process of pumping heated homogeneous solution 24 through the preheating heat exchanger 16 to cool the homogeneous solution 24 and preheat the incoming heterogeneous mixture 12 provides dramatic energy recovery and efficiency. The utilization of preheating heat exchanger 16 in the described system gives an energy efficient process that requires less than 5 megajoules per kilogram of plastic (i.e., <5 MJ/kg of plastic), preferably less than 3 MJ/kg of plastic, in non-renewal energy usage (NREU), as discussed in the example below.

EXAMPLE

One embodiment of the continuous system for depolymerizing plastic illustrated in FIG. 1 included a preheater 16 and a heating chamber 18 plumbed together, along with a heater 20 configured to supply heat to heating chamber 18. The total volume of the system was 800 L. The system was used to depolymerize PET into a reaction product output. It was operated with a feed rate of 2 kg of PET per minute (i.e., 2 kg/min), a flow rate of 20 L of the heterogeneous mixture 12 per minute (20 L/min), and a reaction temperature of 250° C. Various aspects of the system and process were analyzed, including the time required for fluid exiting heating chamber 18 to reach the predetermined reaction temperature, the non-renewable energy usage rate during operation of the system, the reaction product output rate, and the reaction product output composition.

Figure 2:
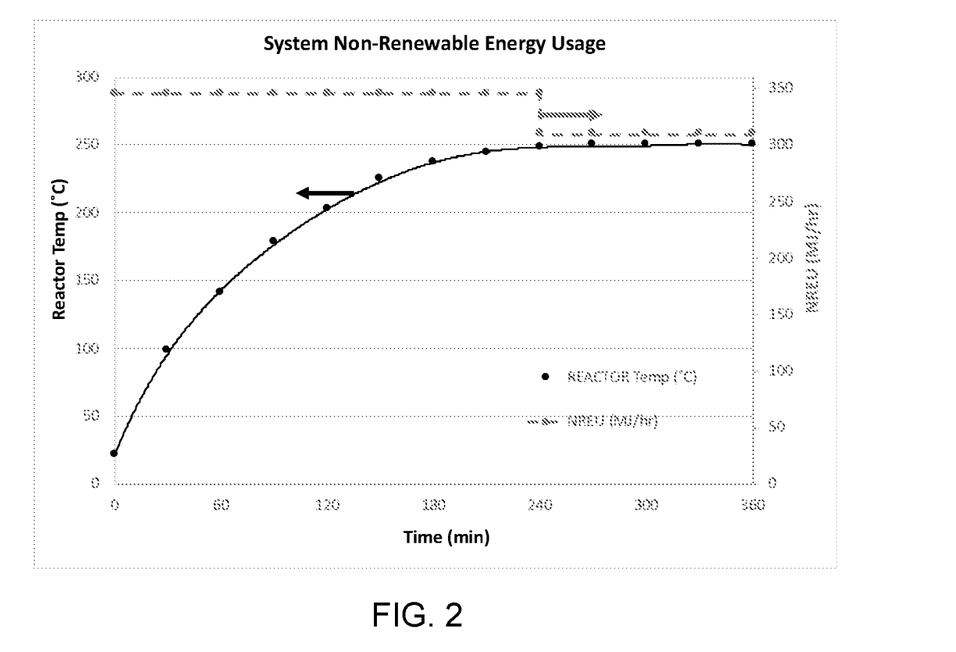
FIG. 2 is a graph illustrating the reduction in non-renewable energy usage (NREU) achieved when an embodiment of the system disclosed herein reaches a steady-state of a continuous process.

FIG. 2 shows the time in which the fluid exiting heating chamber 18 reached the target reaction temperature of 250° C. The system required a warm-up stage in which ethylene glycol was recirculated through preheater 16, heating chamber 18, hold tube 22, then back through the opposite side of preheater 16. The warm-up stage required 240 minutes (4 hours) before the fluid exiting heating chamber 18 reached the desired reaction temperature of 250° C. The heater 20 was a conventional hot oil system (96 kW Mokon HFT system, DELF600 heating fluid), which could only draw a maximum of 96 kW or 345.6 MJ/hr of energy. FIG. 2 shows the heating profile (lower line) of the system over 360 minutes (6 hours). At 240 minutes (4 hours), the system reached steady-state with a consistent temperature of 250° C. in the fluid exiting the heating chamber 18.

FIG. 2 also illustrates the reduction in non-renewable energy usage when the system reached steady-state. Upon reaching steady-state, the heater 20 no longer required maximum energy consumption to maintain the reaction temperature. Instead, the system maintained the reaction temperature by cycling the heater 20 between ON (96 kW) and OFF (0 kW). In steady state, the ON/OFF cycles of heater 20 may range between 30-60 seconds ON and between 2-10 seconds OFF. For example, the heater 20 may cycle between 40 seconds ON and 5 seconds OFF. Because no energy is consumed during the OFF cycle, a reduction of 5-25% in energy consumption was observed when steady state was reached as illustrated by the NREU line (higher line) in FIG. 2. Specifically, a drop in NREU was observed when steady-state was reached 4 hours after heating began. In this system with heater 20 cycling 40 seconds ON and 5 seconds OFF in steady state, the average energy draw was reduced from 96 kW to 85.3 kW (307.2 MJ/hr). This NREU reduction equates to an 11.2% reduction in energy consumption.

Figure 3:
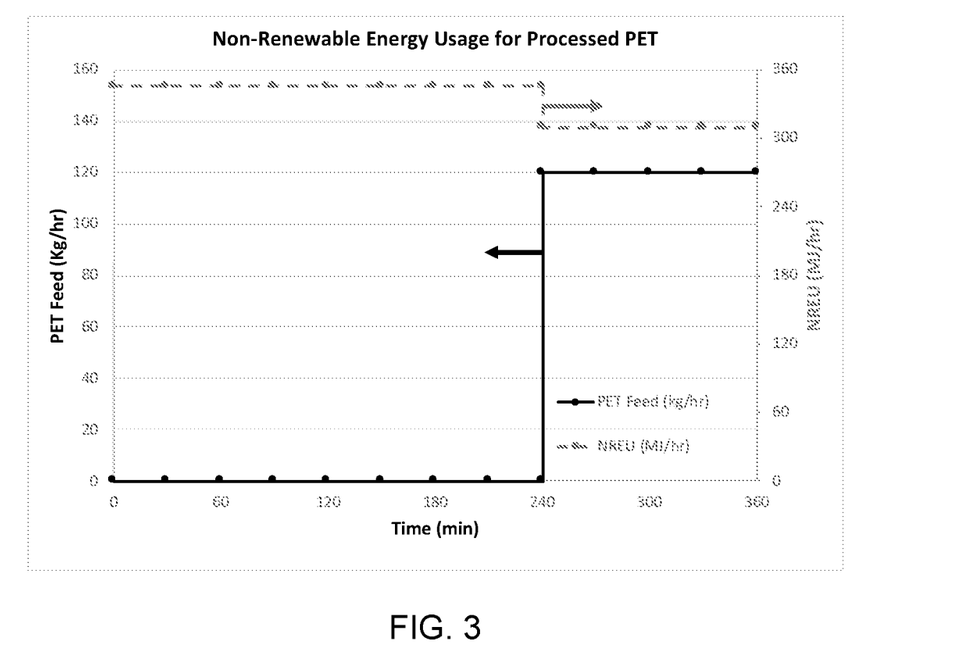
FIG. 3 is a graph illustrating the NREU in relation to a plastic feed rate into an embodiment of the system disclosed herein.

Once the fluid exiting heating chamber 18 reached the target temperature of 250° C., the system was ready for depolymerization. As shown in FIG. 3, PET was fed into the system at a rate of 120 kg/hr beginning at the 4-hour mark. The PET feed rate is represented by the lower line in FIG. 3. A key metric for evaluating system feasibility is the amount of non-renewable energy usage (NREU) needed to depolymerize 1 kilogram of PET. This value is easily calculated by dividing the non-renewable energy consumption (in MJ/hr) during steady state operation of the system by the feed rate of PET (in kg/hr). For this example, dividing the steady-state NREU of 307.2 MJ/hr by the PET feed rate of 120 kg/hr shows that 2.56 MJ of NREU is needed per kilogram of PET depolymerized (or 2.56 MJ/kg PET). This value is calculated while the PET is being fed into the system and omits the initial warm-up stage. The NREU required for warm-up becomes negligible the longer the system operates.

Depolymerization of the heterogeneous mixture containing PET to a homogeneous solution 24 containing the reaction product yields a composition of practical monomers, which can be used to repolymerize PET. The discharge of the reaction product can be monitored using high performance liquid chromatography (HPLC). Samples can be collected from the exiting fluid, such as homogeneous fluid 24 exiting chiller 28, injected on the HPLC, and compared against known monomer standards (e.g., BHET, MHET, TA, etc.) and known monomer concentrations. HPLC analysis was conducted on numerous reaction product samples that were produced using one embodiment of the system for depolymerizing plastic illustrated in FIG. 1, using PET for the plastic feed material and using ethylene glycol for the solvent. Table 1 below provides the compositional make-up of the reaction product samples as measured in these tests.

TABLE 1

| Components in Reaction Product | | Alternate Name | % of Component in Reaction Product |
|---|---|---|---|
| MAJOR | bis(2-Hydroxyethyl) terephthalate | BHET | 85-98% |
| MINOR | 2-hydroxyethyl terephthalic acid | MHET | <10% |
| MINOR | Dimers | Dimer | <10% |
| MINOR | Mixed Ester with DEG | Mixed Ester | <6% |
| TRACE | terephthalic acid | TA | <1% |
| TRACE | Trimers | Trimer | <1% |
| TRACE | higher oligomers | oligos | <1% |

The maximum yield rate of the reaction product can be calculated using the following equation: $Y=FM$, where $Y$ is the maximum yield rate of the reaction product, $F$ is the PET feed rate, and $M$ is the ratio of the major product molecular weight (e.g., BHET mw=254.24 g/mol) to the PET repeat unit molecular weight (mw=192.17 g/mol). If the major product is BHET, then $M$ may be calculated: $M=254.24/192.17=1.323$. For example, if PET feed plastic is fed into the system at a rate of 120 kg/hr, the maximum expected yield would be: $Y=120$ kg/hr*$1.323=158.76$ kg/hr of reaction product. This also amounts to a loss of 38.76 kg of ethylene glycol (34.9 liters) solvent, which is consumed during the reaction and added into the reaction product.

Figure 4:
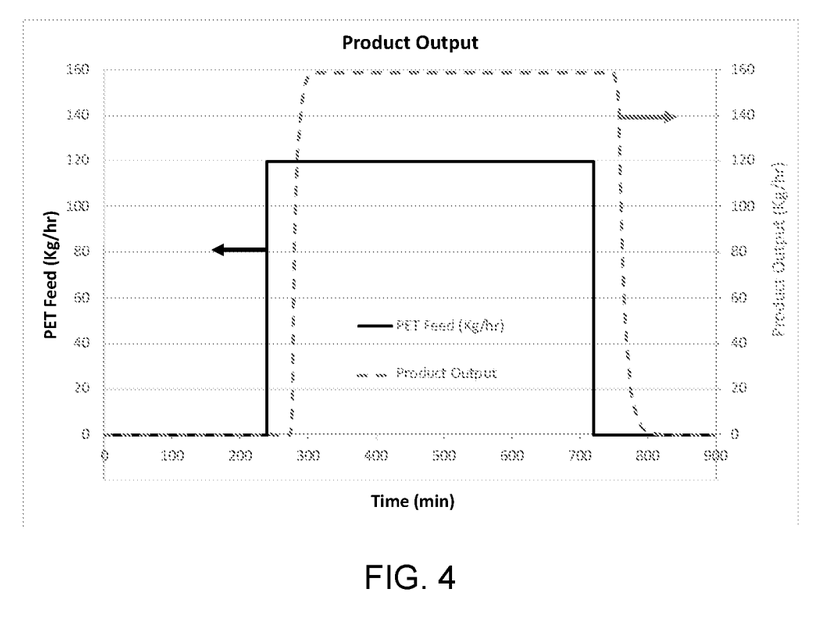
FIG. 4 is a graph illustrating the reaction product output achieved with an embodiment of the depolymerization system and process disclosed herein in relation to the plastic particle feed rate.

FIG. 4 shows the incoming PET feed rate (lower line) and the exiting reaction product rate (upper hashed line) observed with one embodiment of the system for depolymerizing plastic. The data incorporated into FIG. 4 includes a system warm-up between hours 0-4, PET feed between hours 4-12, and reaction product flush/purge between hours 12-15. Since the system is a continuous flow-through system, time is required for the plastic feed material to traverse through the system, convert to the reaction product, and then exit the system for collection. The delay between the initial PET feed and first observance of the reaction product was approximately 40 minutes, equivalent to the full residence time of the system. In other words, it took about 40 minutes for the heterogeneous mixture 12 containing PET to travel through the 800 L system at a flow rate of 20 L/min. However, diffusion effects were apparent before the reaction product reached steady-state and while the reaction product was being flushed/purged from the system. Reaction product output reached a steady-state maximum approximately 60 minutes after the start of the PET feed.

The system and process illustrated in FIG. 1 may also be used to dissolve and purify plastic. The system may be used with various plastics such as, but not limited to, polyethylene, polypropylene, polystyrene, and polyvinyl chloride. Solid plastic particles of these plastics may be mixed with a solvent in mixer 10 to produce a heterogeneous mixture 12. Examples of solvents are, but are not limited to, alcohols, amines, ethers, non-polar aliphatic solvents, non-polar cyclic solvents, non-polar aromatic solvents. As an example, suitable solvents include hexanes, cyclohexane, toluene, xylenes, acetone, and tetrahydrofuran. Pump 14 pumps the heterogeneous mixture 12 through the series of connected lines illustrated in FIG. 1. The pump 14 operates at a particle speed great enough to maintain the particles in suspension in the solvent and to prevent the particles from agglomerating and clogging the lines. By operating continuously without stopping, the pump 14 flows the heterogeneous mixture through the system at a steady rate that makes the conversion of solid plastic into liquefied plastic a function of position within the system rather than a function of time—as in batch systems. The preheating heat exchanger 16 is optionally used to preheat the heterogeneous mixture 12. The preheater 16 may heat the heterogeneous mixture 12 by a heat source. Alternatively, the hot homogeneous solution containing the liquefied plastic after the dissolution can be used in the preheater 16 to transfer heat to the heterogeneous mixture and, in the process, cool itself down. The preheated heterogeneous mixture 12' flows continuously into and through a downstream heating chamber 18 in which dissolution starts. The heating chamber 18 may raise the temperature of the heterogeneous mixture to a dissolution temperature of at least 100° C. The dissolution temperature may be determined based on the melting point of the solid plastic particles. For example, the dissolution temperature may be at least equal to the melting point, at least 10° C. greater than the melting point, or at least 20° C. greater than the melting point. The same heat source options discussed above in connection with the system and process for depolymerizing plastic may be used in connection with the system and process for dissolving plastic. Hold tube 22 maintains the dissolution temperature for at least one minute to complete the conversion of the heterogeneous mixture containing solid plastic to a homogeneous solution 24 containing the liquefied plastic. In other words, the dissolution is completed in the hold tube. The exiting homogeneous solution contains the solvent and the dissolved plastic in the form of a liquefied plastic product. Backpressure regulator 26 maintains a system pressure above the vapor pressure of the solvent at the dissolution temperature. After flowing through the backpressure regulator 26, the homogeneous solution 24 flows through an optional chiller 28 to remove any excess heat that preheater 16 did not reclaim. After the solution is cooled, it is poured into precipitation or crystallization tanks and cooled until the liquefied plastic precipitates as a solid product 34. The solvent is separated from the solid product by decanting, filtering, centrifugation, or distillation. The solid product may be subsequently filter-pressed to further separate it from any remaining solvent. The separated solvent may be recirculated back to mixer 10 for reuse. The optional solvent cleaning step may be used in the system and process for dissolving plastic. Except as otherwise stated, the system and process for dissolving plastic includes the same features and options as the system and process for depolymerizing plastic described above.

Many modifications and other embodiments of the inventions set forth herein will come to mind to one skilled in the art to which these inventions pertain having the benefit of the teaching presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. The scope of the claims is not meant to be limited to the exemplary versions described in detail.

What is claimed is:

1. A continuous flow process for depolymerizing plastic, comprising:
   a) continuously flowing a mixture containing solid plastic particles, a catalyst, and a solvent through a preheating heat exchanger then through a line in a heating chamber; wherein the mixture flows at a rate sufficient to ensure a particle speed of at least 30 cm/s to maintain suspension of the plastic particles in the solvent and to prevent the plastic particles from agglomerating and clogging the line; wherein the plastic particles consist of polyethylene terephthalate, modified polyethylene terephthalate, polyethylene terephthalate blends, Polyethylene naphthalate, polybutylene terephthalate, polyethylene terephthalate glycol, polylactic acid, poly(glycolic acid), poly D,L-lactic-co-glycolic acid, polyethylene 2,5-furandicarboxylate, copolyesters, polycarbonates, polyamides, or any combination thereof; wherein the solvent consists of ethylene glycol, diethylene glycol, glycol ethers, 2-ethyl hexanol, tetramethyl cyclobutanediol, cyclohexanedimethanol, alcohols, ethanol amine, ionic liquids, polar protic solvents, polar aprotic solvents, or any combination thereof;
   b) transferring heat through the line in the heating chamber to heat the mixture to a reaction temperature of at least 150° C. to start the depolymerization of the plastic particles in the solvent into a homogeneous solution including a liquefied reaction product;
   c) holding the mixture at the reaction temperature for at least one minute; and
   d) flowing the homogeneous solution through a passage in the preheating heat exchanger after the homogeneous solution exits the heating chamber; wherein the homogeneous solution transfers heat to the mixture flowing through the preheating heat exchanger to preheat the mixture.

2. The continuous flow process of claim 1, wherein the liquefied reaction product includes monomers, dimers, or oligomers.

3. The continuous flow process of claim 1, wherein the liquefied reaction product includes (bis (2-hydroxyethyl) terephthalate, dimethyl terephthalate, terephthalic acid, (bis (2-hydroxyethyl) naphthalate, (bis (2-hydroxyethyl) Furanoate, their respective oligomers, acids, half-esters, mixed esters, dioctyl terephthalate, diisobutyl terephthalate, dibutyl terephthalate, bisphenol A, lactates, bis (2-hydroxyethyl) terephthalamide, other terephthalamides, or any combination thereof.

4. The continuous flow process of claim 1, wherein the reaction temperature is within 20° C. of the melting point of the plastic particles in the mixture.

5. The continuous flow process of claim 1, wherein the reaction temperature is at least 230° C.

6. The continuous flow process of claim 1, further comprising maintaining a system pressure above the vapor pressure of the solvent at the reaction temperature to prevent the solvent from evaporating.

7. The continuous flow process of claim 1, wherein the catalyst consists of zinc salts, zinc acetate, zinc chloride, titanium salts, titanium (IV) isopropoxide, titanium (IV) n-butoxide, manganese salts, magnesium salts, sodium hydroxide, potassium hydroxide, 1, 5, 7-Triazabicyclo [4.4.0] dec-5-ene, 1, 8-Diazabicyclo [5.4.0] undec-7-ene, magnesium acetate, 4-dimethylaminopyridine, amine, trialkyl amine, or any combination thereof.

8. The continuous flow process of claim 1, further comprising:
   e) cooling the homogeneous solution in a chilling heat exchanger to a temperature below 50° C.;
   f) settling the cooled homogeneous solution at room temperature for a time between about 0.5 hour and 100 hours to allow the liquefied reaction product to solidify into a solid reaction product;
   g) separating the solid reaction product from the solvent by one or more of decanting, filtering, centrifuging, pressing, and distillation; and
   h) reusing the solvent separated from the solid reaction product in the process.

9. The continuous flow process of claim 1, further comprising:
   e) separating the solvent from the reaction product;
   f) removing contaminants from the solvent by filtration or with sorbents; and
   g) reusing the solvent in the process by mixing solid plastic particles in the reused solvent to form the mixture.

10. The continuous flow process of claim 1, wherein the plastic particles have a size between 0.1 μm and 20,000 μm in at least one dimension.

11. The continuous flow process of claim 1, wherein the process reaches a steady state when a temperature of the mixture at a predetermined point in the heating chamber equals the reaction temperature; and wherein in the steady state the process consumes a lower amount of non-renewable energy than during an initial warm-up state.

12. The continuous flow process of claim 11, wherein in the steady state the continuous process consumes less than 5 MJ of non-renewable energy to depolymerize 1 kilogram of solid plastic particles.

13. The continuous flow process of claim 11, wherein in the steady state the continuous process consumes less than 3 MJ of non-renewable energy to depolymerize 1 kilogram of solid plastic particles.

14. The continuous flow process of claim 1, wherein in a steady state a maximum production rate of the liquefied reaction product is calculated using the equation $Y=FM$, where Y is a maximum production rate of the liquefied reaction product, F is the feed rate of the solid plastic particles, and M is the ratio of a major product molecular weight to a plastic repeat unit molecular weight.

15. The continuous flow process of claim 1, wherein the solid plastic particles comprise polyethylene terephthalate; and wherein the liquefied reaction product comprises:
   85% to 98% of bis(2-Hydroxyethyl) terephthalate;
   less than 10% of 2-hydroxyethyl terephthalic acid;
   less than 10% of dimers;
   less than 6% of mixed esters with diethylene glycol;
   less than 1% of terephthalic acid;
   less than 1% of trimers; and
   less than 1% of higher oligomers.

16. A system for continuous depolymerization of plastic, comprising:
   a pump operating at a flow rate;
   a line through which the pump continuously feeds a heterogeneous mixture including solid plastic particles, a catalyst, and a solvent at the flow rate; wherein the flow rate is sufficient to ensure a particle speed of at least 30 cm/s; wherein the plastic particles consist of polyethylene terephthalate, modified polyethylene terephthalate, polyethylene terephthalate blends, polyethylene naphthalate, polybutylene terephthalate, polyethylene terephthalate glycol, polylactic acid, poly(glycolic acid), poly D,L-lactic-co-glycolic acid, polyethylene 2,5-furandicarboxylate, copolyesters, polycarbonates, polyamides, or any combination thereof; wherein the solvent consists of ethylene glycol, diethylene glycol, glycol ethers, 2-ethyl hexanol, tetramethyl cyclobutanediol, cyclohexanedimethanol, alcohols, ethanol amine, ionic liquids, polar protic solvents, polar aprotic solvents, or any combination thereof;

a heating zone raising the temperature of the heterogeneous mixture flowing through the line to a reaction temperature of at least 150° C.; wherein the conversion of the heterogeneous mixture containing the solid plastic particles into a homogeneous solution containing a liquefied reaction product is started in the heating zone;

a hold tube receiving the heated heterogeneous mixture from the heating zone to maintain the reaction temperature for a hold time of at least one minute at the flow rate to complete the conversion of the heterogeneous mixture containing the solid plastic particles into the homogeneous solution containing the liquefied reaction product; and a preheating heat exchanger that preheats the heterogeneous mixture upstream of the heating zone; wherein the preheating heat exchanger preheats the heterogeneous mixture indirectly with the homogeneous solution containing the liquefied reaction product to cool the homogeneous solution.

17. The system of claim 16, further comprising:
a mixer upstream of the heating zone using an agitator or recirculating solvent to stir the heterogeneous mixture.

18. The system of claim 17, wherein the hold tube is an insulated pipe or tubing having a length sufficient to ensure that the conversion of the heterogeneous mixture into the homogeneous solution containing liquefied reaction product is complete.

19. The system of claim 18, wherein the hold time in the hold tube is between 1 minute and 60 minutes.

20. The system of claim 16, further comprising a reactor heat exchanger in the heating zone that raises the temperature of the heterogeneous mixture to the reaction temperature; wherein a heat source is configured to heat a heat transfer fluid that flows past the heterogeneous mixture in the reactor heat exchanger to transfer heat to the heterogeneous mixture.

21. The system of claim 16, further comprising a contaminant removal zone downstream of the heating zone and including a filter or a sorbent, wherein the contaminant removal zone is configured to remove contaminants from the solvent.

22. The system of claim 16, further comprising a chiller downstream of the heating zone and including a chilling heat exchanger with the homogeneous solution on one side cooled indirectly by a cold liquid on the other side of the heat exchanger, wherein the chiller lowers the temperature of the homogeneous solution to below 50° C.

23. The system of claim 16, further comprising a separator that includes a precipitation or crystallization tank in which the liquefied reaction product in the homogeneous solution solidifies into a solid reaction product and precipitates.

24. The system of claim 16, wherein the heating zone includes a heat exchanger; wherein the heat exchanger of the heating zone and the preheating heat exchanger are each a tube-in-shell, tubes-in-shell, coil-in-shell, tube-in-tube, jacketed piping, platular, plate-and-shell, or plate-and-frame heat exchanger.

25. The system of claim 16, wherein the heating zone and the preheating heat exchanger each include multiple lengths of jacketed piping having a jacket around an inner pipe, wherein the jacketed piping is connected.

26. The system of claim 25, wherein the inner diameter of the inner pipe in the jacketed piping is between 1 cm and 100 cm and the diameter of the jacket is between 1.1 and 5.0 times the diameter of the inner pipe.

\* \* \* \* \*